US007728253B2

(12) United States Patent
Hopwood

(10) Patent No.: US 7,728,253 B2
(45) Date of Patent: Jun. 1, 2010

(54) NANO-PARTICLE TRAP USING A MICROPLASMA

(75) Inventor: Jeffrey A. Hopwood, Needham, MA (US)

(73) Assignee: Northeastern University, Boston, MA (US)

( * ) Notice: Subject to any disclaimer, the term of this patent is extended or adjusted under 35 U.S.C. 154(b) by 445 days.

(21) Appl. No.: 11/478,348

(22) Filed: Jun. 29, 2006

(65) Prior Publication Data

US 2010/0072391 A1   Mar. 25, 2010

Related U.S. Application Data

(60) Provisional application No. 60/694,962, filed on Jun. 29, 2005.

(51) Int. Cl.
*B23K 10/00* (2006.01)
(52) U.S. Cl. .............................. 219/121.46; 219/121.59; 219/121.41; 216/59; 156/345.24
(58) Field of Classification Search ............ 219/121.59, 219/121.41, 121.43, 121.45, 121.46; 216/59, 216/60; 156/345.24–345.27; 118/723 R
See application file for complete search history.

(56) References Cited

U.S. PATENT DOCUMENTS

| 5,942,855 | A | 8/1999 | Hopwood | 315/111.51 |
|---|---|---|---|---|
| 5,980,767 | A * | 11/1999 | Koshimizu et al. | 216/60 |
| 6,032,544 | A * | 3/2000 | Harwell et al. | 73/865.5 |
| 6,908,529 | B2 * | 6/2005 | Yamamoto et al. | 156/345.24 |
| 6,917,165 | B2 | 7/2005 | Hopwood et al. | 315/111.21 |
| 6,958,484 | B2 * | 10/2005 | Mitrovic | 250/559.27 |
| 7,101,805 | B2 * | 9/2006 | Johnson et al. | 438/706 |
| 2002/0016068 | A1 * | 2/2002 | Nakano et al. | 438/689 |
| 2002/0163637 | A1 * | 11/2002 | Rossman et al. | 356/237.4 |
| 2004/0031776 | A1 * | 2/2004 | Gevelber et al. | 219/121.36 |
| 2005/0040145 | A1 * | 2/2005 | Okumura et al. | 219/121.56 |
| 2006/0256330 | A1 * | 11/2006 | Leipertz | 356/301 |
| 2006/0289809 | A1 * | 12/2006 | Bonne et al. | 250/504 R |

OTHER PUBLICATIONS

Karanassios, Vassili, "Microplasmas for Chemical Analysis: Analytical Tools or Research Toys?", *Spectrochimica Acta Part B*, vol. 59, pp. 909-928 (2004).

* cited by examiner

*Primary Examiner*—Mark H Paschall
(74) *Attorney, Agent, or Firm*—Weingarten, Schurgin, Gagnebin & Lebovici LLP

(57) ABSTRACT

A system and method employing a microplasma to electrically charge nano- or micro-particles in a gas phase and, subsequently, trap the charged particles within the microplasma using the microplasma's built-in electric fields are disclosed. Confinement of the particles allows their density to be increased over time such that very low concentrations of particles can be detected, e.g., by methods such as laser scattering and/or detection of the plasma-induced charge on the particles. Preferably, charge detection methods are employed when nano-particles are to be trapped and detected.

17 Claims, 13 Drawing Sheets

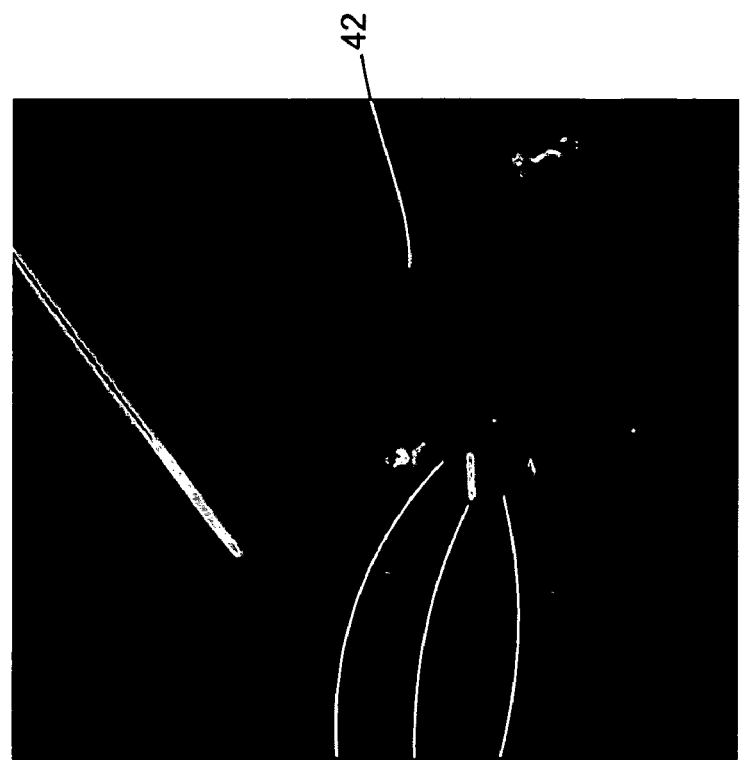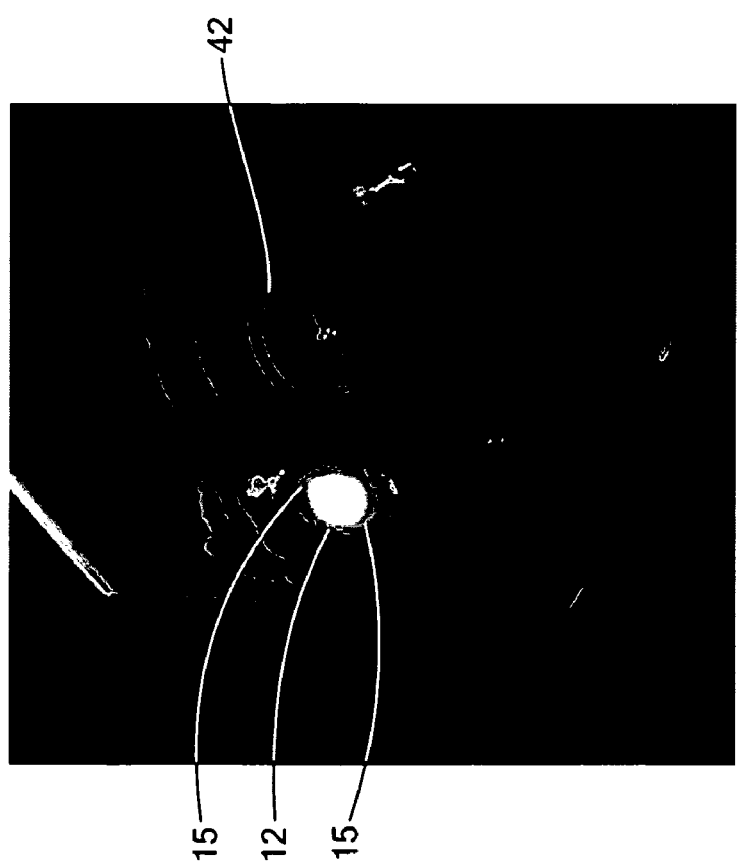
FIG. 4(a)
FIG. 4(b)

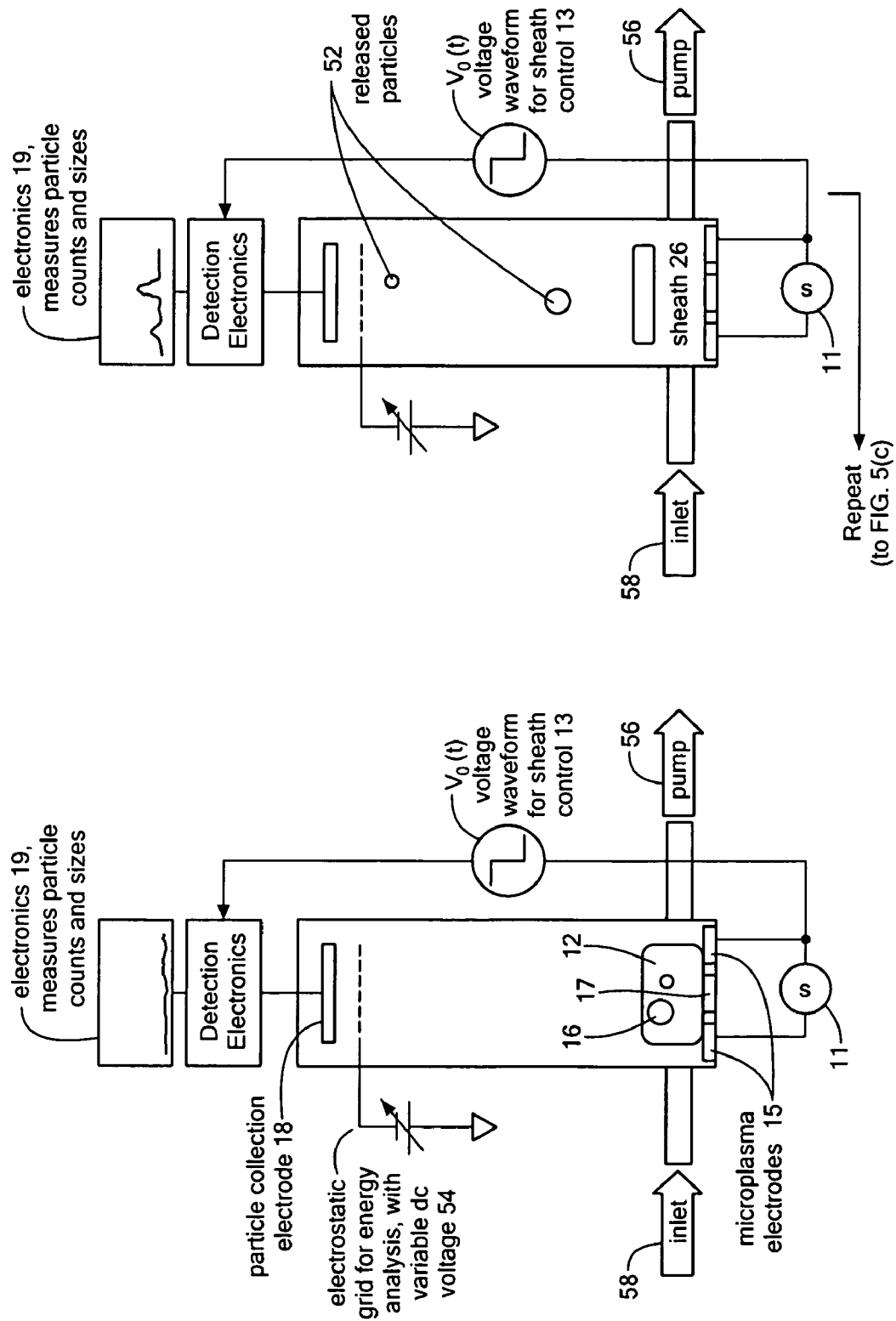

Side view of FIG. 11(a)

Side view of FIG. 11(a)

NANO-PARTICLE TRAP USING A MICROPLASMA

CROSS REFERENCE TO RELATED APPLICATIONS

This application claims the priority of U.S. Provisional Application No. 60/694,962 filed Jun. 29, 2005 entitled, NANO-PARTICLE TRAP USING A MICROPLASMA, the whole of which is hereby incorporated by reference herein.

STATEMENT REGARDING FEDERALLY SPONSORED RESEARCH OR DEVELOPMENT

Part of the work leading to this invention was carried out with United States Government support provided under a grant from the National Science Foundation, Grant No. CCF-0403460. Therefore, the U.S. Government has certain rights in this invention.

BACKGROUND OF THE INVENTION

Very low concentrations of nano-particles, or any other extremely small, gas-borne particles, are difficult to detect due to their small size and low concentrations. There is a basic need for accurate detection of nano-particles in the environment and, in particular, for detection of airborne particles that may affect human health. Detection of nano-particles and the determination of their size distribution is also a critical diagnostic tool for nano-manufacturing processes that are expected to produce close-tolerance nano-particles. Manufacturing processes that use nano-particles as a raw material may also benefit from the development of sensors capable of monitoring the size distribution of the source materials in real time. In addition to near-earth environments, large-scale nano-particle production may impact the upper atmosphere. Here, nano-particles may become electrically charged and suspended in the earth's atmosphere where unanticipated effects (such as catalysis of atmospheric chemical processes) may occur. Finally, trapping and removal of nano-particles will be very beneficial to semiconductor clean-room processes, where the presence of nano-particles is increasingly damaging.

Current detection schemes rely on laser scattering from particles that are entrained in flowing gas samples. Laser scattering techniques are not as effective for small nano-particles because the scattering cross section decreases as the sixth power of the particle radius. In addition, very clean environments have so few particles that traditional methods of particle detection may not detect particles with statistical certainty. Thus, better methods of collecting and detecting small particles are clearly desirable.

BRIEF SUMMARY OF THE INVENTION

The system and method of the invention use a microplasma to electrically charge nano- or micro-particles in a gas phase and, subsequently, trap the charged particles within the microplasma using the microplasma's built-in electric fields. Confinement of the particles allows their density to be increased over time such that very low concentrations of particles can be detected, e.g., by methods such as laser scattering and/or detection of the plasma-induced charge on the particles. Preferably, charge detection methods are employed when nano-particles are to be trapped and detected. Laser scattering techniques are less effective for small nano-particles because the scattering cross section decreases as $a^6$, where a is the particle radius. On the other hand, plasma-induced charge scales as approximately a, making the detection of nano-particles more practical when the pulse charge detection technique according to the invention is incorporated.

Use of a microplasma is an effective method to trap particles in a small volume (<1 mm$^3$) where the concentrated particles can be more robustly counted. "Microplasma" is a broadly used term that applies to many small volume electrical discharges. Typical plasmas have lengths on the order of several centimeters and larger. The term "microplasma" has two commonly used definitions:[1]

"... in a very strict sense of the word, for any device to be called micro-something, at least one of the dimensions must be less than 100 µm. This strict definition was relaxed to include devices that were submillimeter scale and it was adhered to. The definition was further relaxed to include millimeter-size plasmas provided that they were microfabricated."

In the first definition, the length of the plasma's central region is typically measured in units of micrometers. Following this definition, the size of the microplasma is approximately 100 µm or less. It is understood by those skilled in the art that the plasma boundary is often not well-defined and that significant ionization of the gas may extend well beyond this 100 µm boundary, however. A second definition of microplasma refers to a gas plasma that is generated by a device that is microfabricated or micromachined, often using the techniques employed by the electronics industry. The so-called micromachined plasma generator often has plasma dimensions that are somewhat greater than one millimeter. In the system and method of the present invention, both definitions of microplasma are included.

In the present invention, the role of the microplasma is to trap and concentrate gas-borne particles into a small volume. This small volume is the central volume of the microplasma. Those skilled in the art will recognize that particle-particle repulsion will limit the number of particles per unit volume within a plasma. Therefore, the precise dimensions and volume of the microplasma are a function of the number of particles one desires to trap within the microplasma. The trade-off is that a large plasma will be capable of trapping a large number of particles, but the particles will not be as localized in space. This non-localization within larger volume plasmas may degrade the performance of particle sensing.

Thus, in one aspect, the invention is directed to a system for detection of particles in a gas, the system including a trap microplasma generator trap and a particle sensor. Preferably, the microplasma generator is a portable, low power generator, such as a split-ring resonator. Alternatively, the microplasma generator can be a miniature, e.g., a monolithic, inductively coupled plasma generator. Preferably, the particle sensor detects collected particles by charge. Alternatively, the particle sensor is a scattering laser detector or a differential mobility detector. The sensor can also detect collected particles by light emissions from the particles or from atoms and molecules eroded from the particles.

The method according to the invention includes providing a microplasma generator; forming, a microscopic glow discharge (a microplasma) with the generator; feeding the microplasma with a sample of gas from the gas phase so as to negatively charge, trap and concentrate within said microplasma particles in the vicinity of the microplasma. As a final step, the particles trapped within the microplasma are detected, e.g., by methods that rely on their mass or charge. Preferably, the detecting step includes the steps of applying a voltage waveform to the microplasma and collecting on an electrode the charged particles that have been emptied from the microplasma by the voltage waveform. Exemplary waveforms are a pulse, a ramp and a sinusoid. The detecting step can also include the steps of modulating the power supplied to the microplasma generator, e.g., by turning the power off, so that the microplasma dissipates; and then collecting charged particles emptied from the dissipated microplasma on an electrode.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings, in which:

FIGS. 4a and 4b are micrographs showing microplasma operation in a 99.9% Ar-0.1% $N_2$ discharge at 0.3 W;

FIGS. 5a-5d are schematic views of the system of the invention before (t<0) (5a and 5c) and after (t>0) (5b and 5d) the microplasma particle trap is emptied by pulsing the plasma sheath width;

DETAILED DESCRIPTION OF THE INVENTION

Nano-particles are difficult to measure quickly due to their extremely small size. As nano-technology becomes a reality, however, the accurate and rapid sensing of nano-particles, as well as other sizes of small particles, becomes an important part of many manufacturing processes. Controlling the density and size distribution of nano-particles is not only key for reliable manufacturing, but also critical to the health and safety of the workforce. The preferred system according to the invention consists to two components: a nano-particle trap and a nano-particle sensor. The trap uses a small region of ionized gas (i.e., a microplasma) to negatively charge nearby nano-particles. Once a particle is charged, it is trapped by the voltage gradient within the microplasma. Next, the accumulated nano-particles are detected, preferably by using a voltage of the desired waveform on an auxiliary electrode to empty particles from the trap. Examples of useful waveforms include a pulse, a ramp and a sinusoid. In this embodiment, the charged particles emptied from the trap are collected by an electrode that senses both the accumulated charge on the particles and the time-of-flight between the microplasma and the sensing electrode. These data allow the density and size of the particles to be determined.

Figure 1:
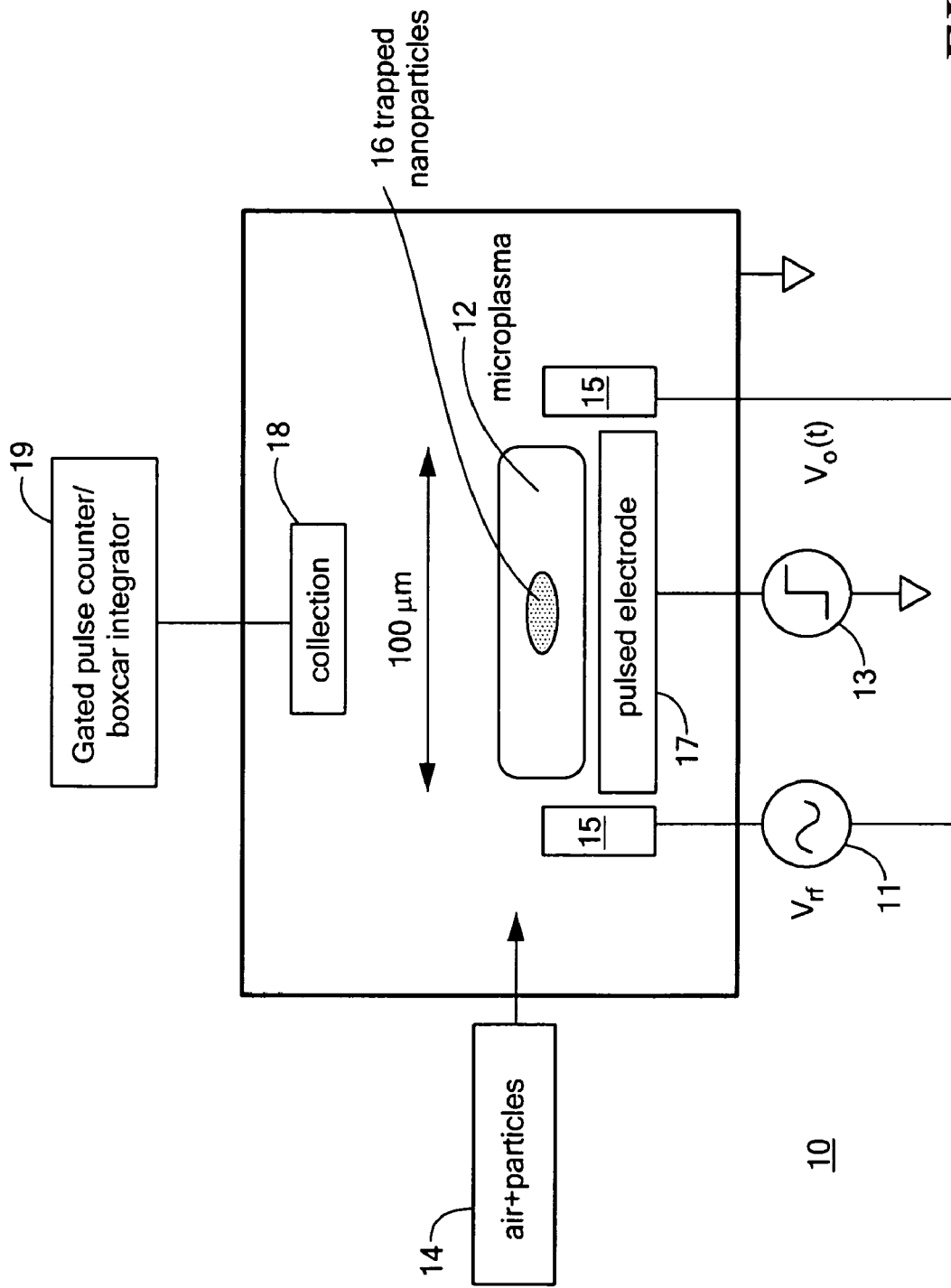
FIG. 1 is a schematic view of the system according to the invention.

The first part of the system consists of a microdischarge (or microplasma) that acts as a nano-particle trap. A simplified schematic view of a nano-particle trap 10 is shown in FIG. 1. The microplasma 12 is typically formed between to microelectrodes 15 using a voltage source $V_{rf}$ 11. Following creation of the microplasma 12 (as will be described further below), nano-particles in the vicinity of the microplasma become negatively charged, and the ambient gas, e.g., air, and associated particles 14 flow into the trap 10. Periodically, the particle trap 10 is emptied by rapidly increasing the ion sheath width (i.e., the dark space) of the microplasma 12 and sweeping the trapped nano-particles 16 toward a collection electrode 18. Depending on the specific voltage waveform 13 that is applied to auxiliary electrode 17 to increase the sheath width, the particles are sorted either by mass or by accumulated negative charge. The total particle count and the size distribution function can then be determined either by time-of-flight measurements or by retarding-potential energy analysis of the particle flux using collection electrode 18 and pulse counting electronics 19.

Particle detection methods known in the art and employable in the system and method of the invention, depending, e.g., on the size of the collected particles, can be grouped as either ex situ or in situ. Ex situ techniques involve laboriously collecting particles on a substrate or grid, and then examining the substrate using SEM, TEM, AFM, laser scattering, etc.[2,3,4] From some of these diagnostics, the size distribution of collected particles can be determined and, with some extrapolation, the in situ nano-particle density may be estimated. The ex situ techniques are expensive and do not provide real-time data, but particle sizes of less than 1 nm are detectable if real-time data are not needed.

This invention focuses primarily on the use of in situ particle detection. Currently, principal in situ methods for particle counting are based on laser light scattering (LLS)[5,8] and laser-induced incandescence (LII).[6] LLS typically uses an argon ion laser (~1 @ 514.4 nm) to illuminate particles. Scattered light is detected by a simple video camera, a photodiode, or by a photomultiplier if high sensitivity to small particles is required. The particles' size distribution is not directly revealed by this technique, although some indication of the particle size may be inferred from the intensity of scattered light, which strongly scales with particle radius as ~$a^6$. The sixth power in the scaling relation makes detection of true nanometer-scale particles difficult. For example, the LLS technique[13] was used to measure particles as small as 16 nm, but it was necessary for the gas-borne nano-particle density to be quite high (~$10^6$ cm$^{-3}$). Alternately, condensation of alcohol on a particle is used to increase the size of nanoparticles (a>10 nm→a>100 nm) such that these small particles are optically detectable, but accurate size distribution information is lost.

Size distributions for populations of nano-particles may be measured by a nano-scale differential mobility analyzer (DMA).[7] The principle of operation uses a gas flow between two electrically-biased coaxial electrodes. Singly charged nano-particles are created by a radioactive Kr-85 source. Nano-particles of high mobility are separated from the flow by the radial electric field, and nano-particles that remain entrapped in the flow are quantified by a condensation particle counter. The technique is widely used, but data acquisition is quite slow due to the long transit time of particles in the DMA.

In LII, the measured decay time of incandescence from laser-heated nano-particles is used. This widely used technique, in combination with SEM-based calibration, is able to determine the monodispersed particle size in a low pressure gas,[6] but is not capable of measuring size distributions. Both LLS and LII detection techniques are suitable for rapid in situ measurements of large nano-particles, but neither method is useful for low density measurements of nanometer-size particles. Neither can the distribution of particle radii be accurately measured.

In addition to measuring light emitted from particles by LII, it is also possible to detect the chemical composition of particles within a plasma by measuring the spectrum of light emitted from atoms and molecules that are eroded from the particles by the plasma. This method can provide information on the chemical composition of the particles. For accurate detection of both the number density and size distribution of true nano-particles, the preferred detection method in the system and method of the invention is by voltage pulsing, release and electrode sensing of the trapped particles, as described above.

The nucleation, trapping, and growth of particulates in gaseous plasmas have been intensely studied in recent years.[8] A prime motivator of this research is the elimination of particles from plasmas that are used in the fabrication of integrated circuits. For these plasmas, the formation and trapping of nano- and microscale particulate matter results in catastrophic failure of the integrated circuit.

Isolated bodies in an electropositive plasma are well-known to accumulate negative charges. This is because free electrons (−) in a plasma have much higher mobility than the positive ions (+). The collection of electrons on the surface of a particle proceeds until the surface is sufficiently negative that additional electrons are electrostatically repelled. In the steady-state, the fluxes of electrons and positive ions to a nano-particle must balance. This observation leads to the commonly used (although somewhat oversimplified[9,10]) expression for the charge on a particle immersed in a plasma with density $n_e$ and electron temperature $T_e$, $$\sqrt{\frac{T_e m_i}{T_i m_e}} \exp\left(\frac{-e^2 Z_d}{4\pi\varepsilon_0 a k_B T_e}\right) = \left(1 + \frac{Z_d n_d}{n_e}\right)\left(1 + \frac{e^2 Z_d}{4\pi\varepsilon_0 a k_B T_i}\right),$$

where $Z_d$ is the charge on a particle in units of electron charges and a is the radius of the nano-particle.[11] Note that this expression ignores photo-ionization of the particle, which may reduce the number of negative charges. From this implicit equation it is possible to observe that the charge on a particle is proportional to the particle radius ($Z_d/a \cong$ const.) provided that the charge density of nano-particles is much less than the electron density ($Z_d n_d \ll n_e$). Table I below shows the calculated number of electrons on a particle of radius a as a function of electron temperature of the plasma. As an example, a 10 nm particle will accumulate ~49 excess electrons in a 3 eV plasma.

TABLE 1

Approximate charge on a nano-particle with radius a (nm) trapped in a plasma with electron temperature $T_e$ (eV)

| $T_e$ (eV) | Approx. Number of Charges ($Z_d$) |
|---|---|
| 1 | 1.9a |
| 2 | 3.5a |
| 3 | 4.9a |
| 4 | 6.3a |
| 5 | 7.6a |

A plasma-immersed nano-particle is subject to at least six different forces.[5,9,12] Of these, the most relevant to the operation of the system of the invention is the electric field force: $F_E = (eZ_d)*E \sim a$. This force is directly proportional to the number of electrons on the particle ($Z_d$) which has been shown to be proportional to the particle radius: $F_E \sim a$.

The molecular drag force is: $F_{drag} \sim n_n v_{rel} m_n (\pi a^2) \sim a^2$. Molecular drag is due to collisions between the particle and gas molecules with a relative velocity $v_{rel}$. This force becomes dominant for high neutral gas density ($n_n$) and for particles with large cross sectional areas ($\pi a^2$). Notice that for nanometer-sized particles at low pressure, the electric field force dominates.

The ion drag force is: $F_{ion} \sim n_i v_i (\pi a^2) \sim a^2$. Ion drag is similar to molecular drag except that the ions exert a longer-range electrostatic force than the neutrals. Therefore, a complete theoretical development would include orbital motion of the ions about the particle. In addition, the ion drag term is often greater than the molecular drag term in a plasma due to the high drift velocity of ions from the center of the discharge toward the walls.

Gravitational force is: $F_g = mg \sim a^3$. Because it is directly proportional to the particle mass, the gravitational force scales as the particle radius cubed. For micron-sized particles, gravity is a significant force but nanometer scale particles are negligibly affected by gravity. Thermophoresis may also be neglected if the microplasma's gas temperature is low.

Figure 2:
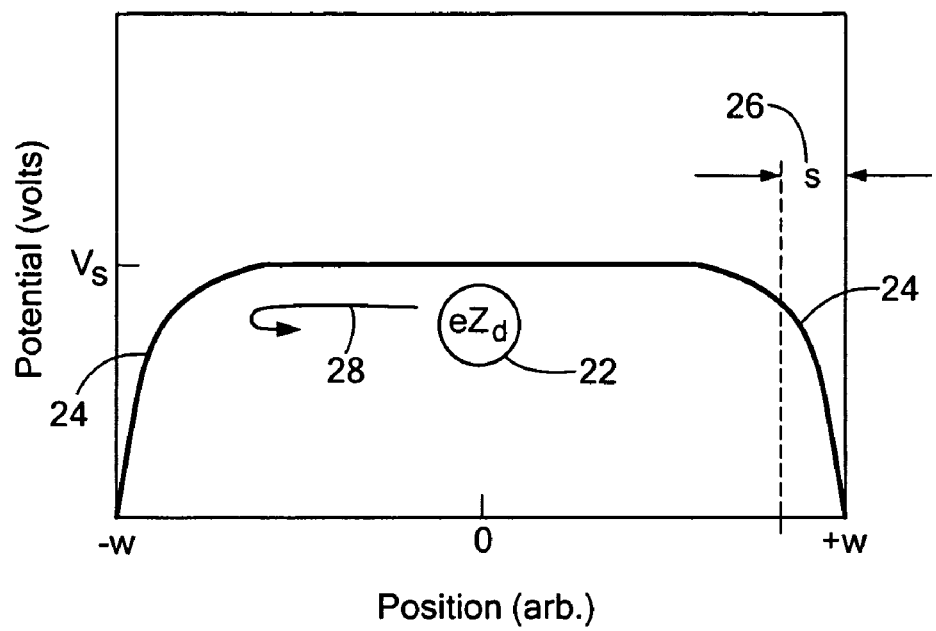
FIG. 2 is a representation of the electrostatic potential (as volts vs. arbitrary position) within a glow discharge (conventional plasma) demonstrating the trapping of a negatively charged nano-particle.

The electrostatic potential within a plasma is strongly influenced by the loss of the highly mobile electrons. The loss of electrons causes the bulk region of the plasma to develop a higher potential ($V_s$) relative to the plasma chamber. In the vicinity of the chamber walls, the plasma is nearly devoid of electrons, giving rise to the dark space or ion sheath (s). In this region, the electric potential increases rapidly due to the depletion of electrons ($n_e \ll n_i$). FIG. 2 is a graph showing the potential well formed inside a typical low pressure glow discharge (w~5 cm, substantially larger than s) and the behavior of a nano-particle.

As illustrated in FIG. 2, a negatively charged nano-particle 22 is trapped within a discharge due to the electric field force exerted by the potential gradient 24 in the plasma. As the particle approaches the sheath region 26, the strong E-field 28 reverses its motion. As previously discussed, large particles (a>100 nm) are subjected to stronger ion drag forces. As a result, the flux of ions from the center of the discharge to the edge causes a net outward force on these large particles that traps them near the sheath edge where the electrostatic and ion drag forces are balanced. Because the ion drag force is proportional to $a^2$, however, particles less than ~50 nm tend to be more uniformly dispersed in the central volume of the plasma.[13]

Finally, large particles can be influenced by gravitational force ($F\sim a^3$) and have been observed to accumulate in the lower sheath regions. In addition, high gas flow rates have been observed to move micron-sized particles out of electrostatic traps if the molecular drag force ($\sim a^2$) exceeds the electrostatic force ($\sim a$). In both of these cases, the higher order forces ($a^2$, $a^3$) become negligible for true nano-particles.

Figure 3:
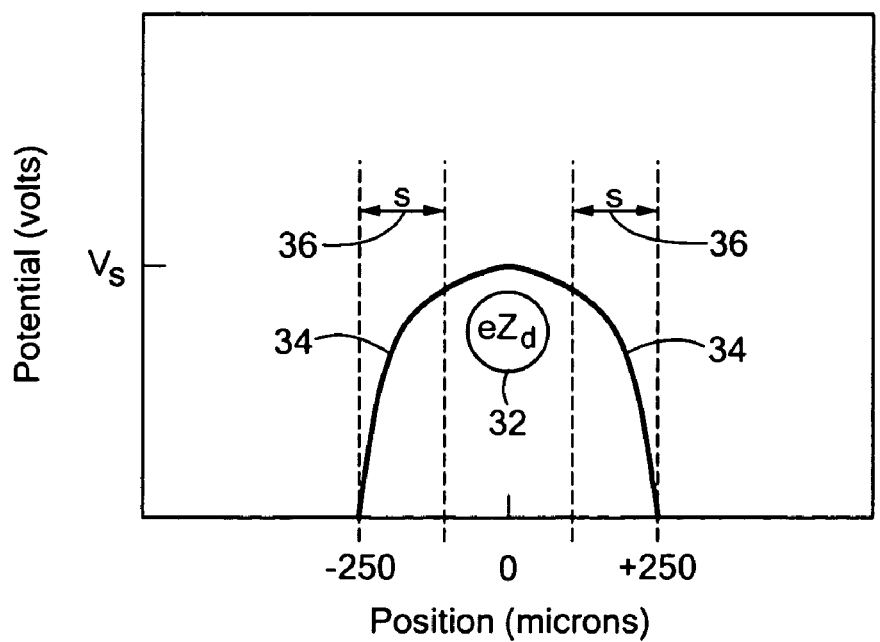
FIG. 3 is a representation of the electrostatic potential (as volts vs. position) showing both trapping and localization (charge=$eZ_d$<0) of nano-particles by a 500 µm-wide microplasma.
Figure 6:
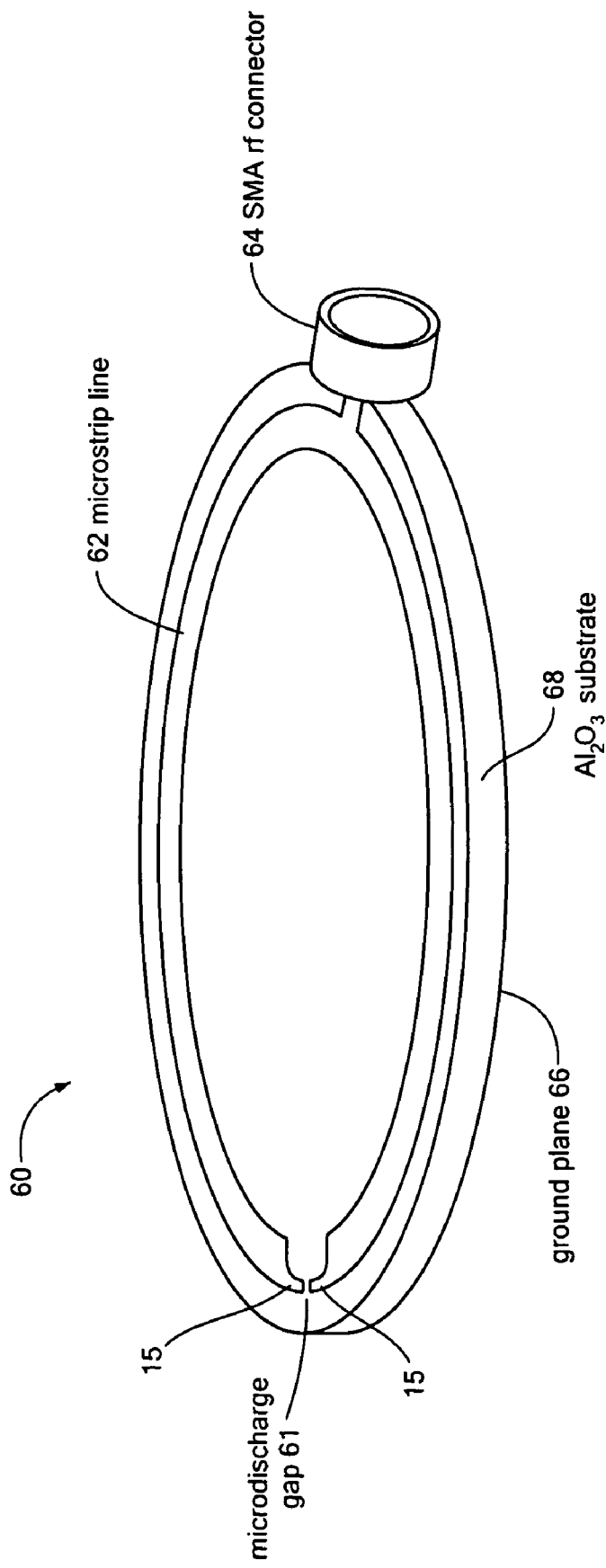
FIG. 6 shows a split-ring resonator (SRR) microplasma device.

In reduction of the invention to practice, a microplasma source was developed that creates a 500 μm-wide discharge using ~0.3 W of power (at 900 MHz).[14] In an exemplary embodiment shown in the micrographs of FIGS. 4a and 4b and in the schematic view of FIG. 6, the discharge is formed in a micromachined gap 61 at the maximum E-field region of a split-ring resonator. The resonator consists of a λ/2 microstrip transmission line in the shape of a ring 62. By appropriate design of the discharge region, this microplasma can operate in argon, oxygen, nitrogen, helium, air and most other gases from less than 0.1 torr to more than atmospheric pressure. Because the sheath width(s) depends primarily on electron temperature and ion density, the sheath regions do not scale down inside a microplasma. As a result, the central plasma region, which is the nano-particle trap, becomes very narrow (e.g., <300 μm), and the particles are well-localized. Twenty-five and 50 μm-wide microplasma have also been developed. Referring to FIG. 3, the localization gained by using a microplasma can be seen. A representative particle 32 is shown localized in the vicinity of the center of the microplasma, between position r=−100 microns and r=+100 microns. The negative charge on the particle ($eZ_d$) prevents the particle from entering the sheath region 36, due to the gradient of the electrical potential 34.

The apparatus for generating a 50-μm wide microdischarge is shown in the micrographs of FIGS. 4a and 4b. In FIG. 4a, the microdischarge 12 is the bright glow that can be seen between the two microplasma electrodes 15 that terminate the circular microstrip transmission line (split-ring resonator), described schematically in FIG. 6. Although the central microdischarge is only 50 μm in width, the microplasma extends beyond this region by several millimeters at lower gas pressure (<100 torr) due to diffusion of charged species and fringing electric fields. The coiled microstrip line structure 42 shown in the middle of the ring (FIGS. 4a and 4b) is a λ/4 transmission line that allows the ring to be DC grounded. This establishes the reference potential that is necessary for pulsing the plasma sheath voltage. FIG. 4b shows the same microplasma generator and microplasma as FIG. 4a, except that the gas pressure is now increased to 100 torr or greater. In this case, the glow of the microplasma 12 is more strongly confined to the central region, although experiments have demonstrated a non-zero electron density several centimeters from the central glow.

A matrix sheath, in which the ions are assumed to be immobile, is used for initial calculations due to its simplicity. A more thorough analysis would use a Child Law sheath or a collisional Child Law sheath that includes collisional ion motion.[15] The high voltage matrix sheath width is a function of applied voltage and plasma electron density. It is given by:

$$s = \left(\frac{2\varepsilon_o V_o}{en_e}\right)^{1/2}.$$

With no applied voltage, the sheath thickness is several Debye lengths, or ~100 μm for $n_e=10^{11}$ cm$^{-3}$. So, for an illustrative sheath expansion to 500 μm, an external voltage of $V_o$ ~200 volts is required. It will be recognized by those skilled in plasma sheath formation that lower voltages are required if the microplasma is less dense. The density can be reduced by decreasing the power absorbed by the microplasma.

Depending on the nature of the information to be extracted from use of the system, two methods of applying $V_o(t)$ to detect nano-particles are contemplated:

A fast rising pulse: This voltage pulse rapidly expands the sheath and accelerates the electrons from the region 100 μm<x<500 μm, but leaves the massive, negatively charged nano-particles behind. These particles are subsequently accelerated by the potential difference that exists within the expanded sheath [δV=V(500 μm)−V(100 μm)] to a kinetic energy that depends on the total charge of the nano-particle [$E=(eZ_d)$ δV]. Detection of particle charge, and hence the particle's radius (recall that $Z_d\sim a$), can be achieved by energy selective particle collection, i.e., by applying known deceleration potentials to the collection probe. Alternately, each nano-particle's velocity will depend on the total charge (~a) and mass (m~$a^3$). Therefore, the size distribution of nano-particles may also be inferred from the time of flight of the particles from the microplasma trap to the collection probe: the collisionless particle velocity scales as $v_0\sim a^{-1}$.

The fast-pulse method of extracting nano-particles from the trap is actually more dynamic than outlined above. Once the sheath has expanded, the equilibrium between electron and ion fluxes to the particle is changed. The nano-particle will collect positive ions as it is accelerated from the sheath. In the limit of a thick sheath, the ion may lose a substantial amount of its negative charge.

A slowly-rising voltage ramp: In this case, the sheath boundary expands more gradually such that nano-particles (and electrons) are moved toward the collection electrode at the velocity of the sheath edge. Because the nano-particles remain near the presheath region, the partial neutralization of charge is avoided, as discussed above. For a simple ramp voltage $V_o(t)=At$, the sheath edge velocity at $t=t_0$ is given by the time derivative of the sheath width, s:

$$\left.\frac{ds}{dt}\right|_{t_0} = \left(\frac{A\varepsilon_o}{2en_e}\right)^{1/2} t_o^{-1/2} = v_o$$

In the limit of a slowly ramped sheath width, all nano-particles have the same velocity ($v_o$), independent of their total charge or mass. The kinetic energy (KE=(½)m$v_o^2$) of the particles, however, varies because the KE is directly proportional to mass. Ignoring collisions with the background gas, all nano-particles arrive at the collection electrode simultaneously. The distribution of particle masses can then be determined by energy-selective collection using retarding potentials on the probe.

The above analysis is correct in the limit that the background gas pressure is low or the microplasma-to-probe separation is small such that molecular drag on the nano-particles can be ignored during the transit period. It may be possible, however, to take advantage of molecular drag to segregate nano-particles by cross sectional area ($a^2$). Again, for the case of a slowly-expanding sheath, it is assumed that all particles are accelerated to the same initial velocity. Next, as the particles traverse the background gas, each particle experiences a molecular drag force that is proportional to the particle cross section, relative velocity, and gas density: $F_{drag}\sim n_n v_{rel}(\pi a^2)$ ~$a^2$. Larger particles are decelerated more rapidly and arrive at the collection electrode later than small particles.

Detection of nano-particles can preferably include both energy analysis and time-of-flight methods as shown in FIGS. 5a-5d. This series of Figs. depicts exemplary implementations of a microplasma particle trap, the size distribution of the trapped particles being detected by sensing the particles' charge, kinetic energy, and time-of-flight. For energy analysis, the collection electrode (probe) 18 is biased with a DC potential such that nano-particles are selectively deflected based on kinetic energy. The addition of a fine, conducting electrostatic grid or mesh 52 may be useful for energy analysis or to deflect electrons or ions using a vatiable dc voltage source 54. Time-of-flight detection of nano-particles is accomplished, for example, by gated pulse counting and boxcar integration of repetitive pulses to the sheath electrode 19.

Figures 5A, 5B:
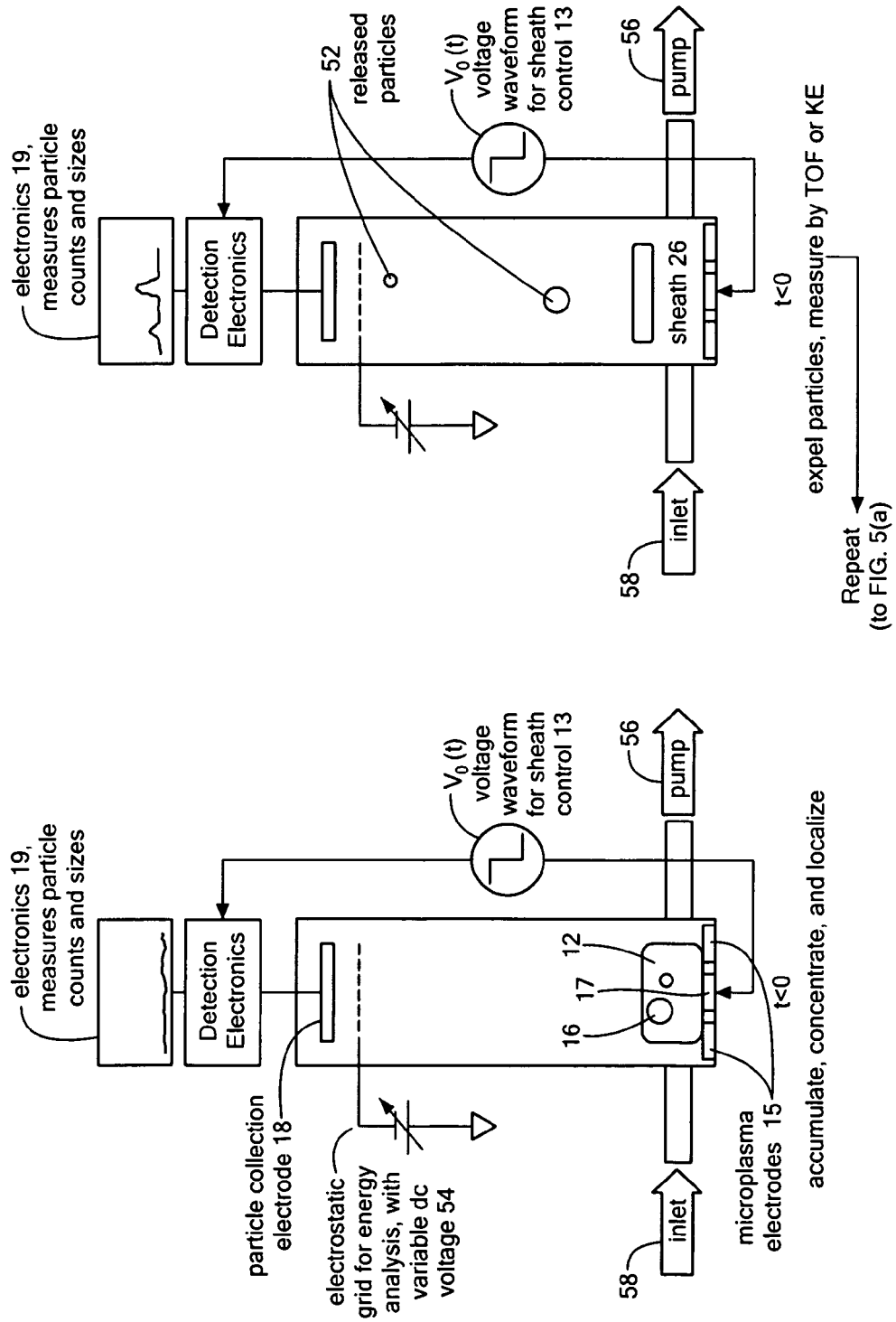

Referring still to FIGS. 5a-5d, particles are transported into the trap via a gas feed within a tube 58 attached to the inlet of the particle sensor. It should be noted that the particles do not necessarily needed to be transported within an inlet tube, however. Particles emerge from the inlet and are charged by electrons generated by the microplasma. The particles are subsequently trapped within the central core of the microplasma 12. In this example, the trap is emptied at the arbitrary time t=0, as shown in FIGS. 5b and 5d. Therefore, the particles are trapped and concentrated from the time that the microplasma is initiated until t=0, as shown in FIGS. 5a and 5c, allowing an arbitrarily large number of particles to be trapped. When the trap is sufficiently filled (i.e., at t=0), the sheath 26 of the microplasma is expanded by applying an appropriately shaped voltage waveform to the electrodes. This forces the particles collected in the trap to be expelled.

Two methods of expanding the sheath are illustrated in FIGS. 5a-5b and FIGS. 5c-5d, respectively. In FIGS. 5a-5b, the sheath control voltage 13 is applied directly to the auxiliary electrode 17, which is immersed in the microplasma 12 sustained by microplasma electrodes 15. FIGS. 5c-5d show that the sheath control voltage may be applied directly to the microplasma electrodes 15, and the auxiliary electrode 17 may be held at a constant potential (here shown as grounded). Those skilled in plasma science will also recognize that the plasma sheath expands as the plasma density decays, so simply decreasing the electron density of the microplasma or decreasing the microplasma's input power will also empty the particle trap, the most simple method being the extinction of the plasma. In FIGS. 5b and 5d the particles have been expelled 52 from the particle trap via the indicated method. The empty trap can then be refilled by newly arriving particles. The population of expelled particles can be sensed by the charge accumulated on the particles' surface using a collection electrode 18, possible in combination with a biased, electrostatic grid 54. The size distribution of the collected particles may be determined by the time-of-flight from microplasma to the collection electrode, by the kinetic energy of the particles, or by other particle detection techniques described in the literature.

Figure 8:
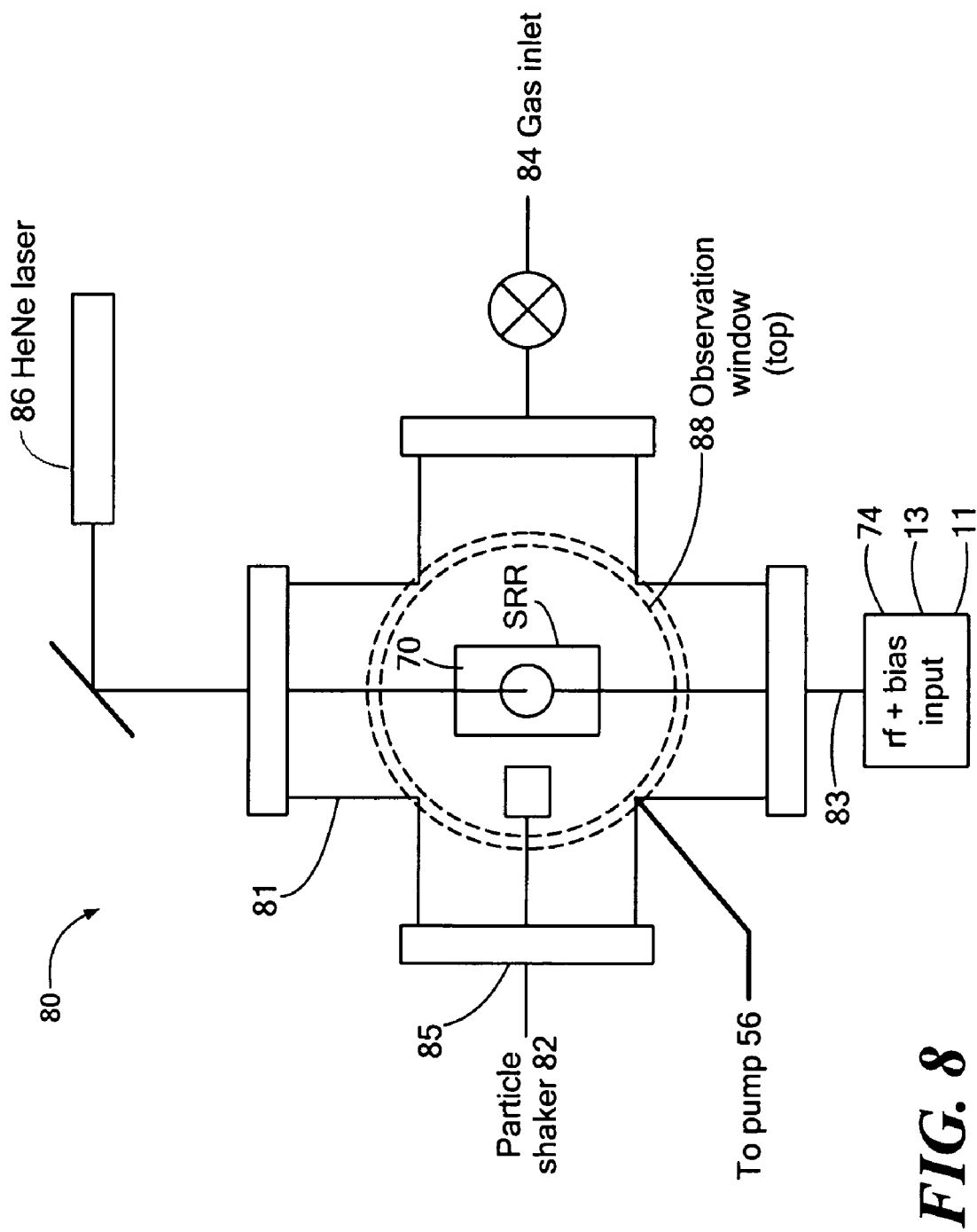
FIG. 8 shows a top view of a microplasma particle trap according to the invention.

To use a complete, portable system of the invention involves simply placing the device, consisting of the particle trap (in the form of a microplasma generator) and detector (or particle sensor), in the environment to be monitored. The placement can be, e.g., in a tube of flowing gas (as shown in FIGS. 5a-5d), within a chamber (as shown in FIG. 8) that is large in reference to the size of the microplasma, or in any appropriate setting, e.g., within a work place, on a person, in the outside environment, in the upper atmosphere, in planetary environments, or outer space. The operator selects an appropriate sampling period during which particles will be trapped, ensuring that the period is sufficiently long to trap enough particles to be sensed. The means of implementing an appropriate method of particle detection (e.g., time-of-flight, particle charge, electrostatic energy analysis, light scattering, optical emission, laser induced incandescence, etc.) is established as part of the instrument such that the detection method is consistent with the desired data. Then, the instrument continuously cycles through the accumulate (FIGS. 5a and 5c) and empty (FIGS. 5b and 5d) modes. The particle data describing the operating environment of the devices are fully updated each accumulate/empty cycle.

The following examples are presented to illustrate the advantages of the present invention and to assist one of ordinary skill in making and using the same. These examples are not intended in any way otherwise to limit the scope of the disclosure.

EXAMPLE I

Microplasma Generation

FIG. 6 illustrates a split-ring resonator (SRR) microplasma source 60 as used in the system of the invention. The microplasma is generated in a micromachined discharge gap 61 formed in a ring-shaped microstrip transmission line 62. The transmission line is formed from a 20 mm diameter gold trace that was photolithographically defined on a 29 mm-diameter $Al_2O_3$ substrate 68. Aluminum oxide was chosen for its chemical resistance to plasma radicals, its high dielectric constant, and good thermal conductivity. The backside of the substrate forms the ground plane 66 of the microstrip transmission line. The high dielectric constant of the substrate ($\in$=9.8) reduces the wavelength of the 900 MHz excitation potential such that the circumference of the ring is exactly one-half wavelength. Therefore, when the electrical potential of the microplasma electrode 15 at one side of the gap 61 is maximum, the electrical potential of the microplasma electrode 15 at the opposite side of the gap 61 is minimum. If the SRR is excited at its resonance frequency, the voltage across the gap prior to plasma ignition is given as:[16]

$$V_{gap} = 4\sqrt{\frac{Z_o Q P_{abs}}{\pi}} \quad (1)$$

where $Z_o$ is the characteristic impedance of the transmission line (70Ω), Q is the quality factor of the resonator (Q=140) and $P_{abs}$ is the power absorbed in watts. The minimum power required to ignite this plasma in air is 3 W, which corresponds to 390 volts across the gap. Once the plasma is lit, however, the plasma resistance loads the split-ring resonator, decreasing Q, and the peak gap voltage decreases to ~100 V. This corresponds to a peak electric field of 4 MV/m and E/p=50 V $cm^{-1}$ $torr^{-1}$. In addition, the pd product for this microdischarge gap is 2 torr-cm, near the minimum of the DC Paschen curve.

For portable operation, microwave power from a cell phone power amplifier chip is introduced to the SRR through a subminiature type-A (SMA) rf connector 64 placed at an appropriate angle relative to the discharge gap)(170° such that the input impedance of the device is 50Ω. The plasma is self-igniting and operates in open laboratory air with no need for external gas flow to stabilize the microplasma.

EXAMPLE II

Particle Trapping

The dynamics of particles in typical plasmas have been studied extensively during the past decade.[17] In this Example, the feasibility of trapping and sorting nano-particles using a microplasma was examined. The motivation for using a microplasma was based on the knowledge that the small size of the microplasma would not only trap, but also concentrate, the particles in a small volume (<<1 mm$^3$); the charging of the particle by the microplasma would allow sorting by both net charge and by particle mobility (e.g., time of flight); and use of the microplasma would allow the creation of a portable detection device.

The microplasma source 70 used in this Example (see FIG. 7) was based on the split-ring resonator describe in Example I but included the addition of two grounded auxiliary electrodes 72 made from λ/4 transmission lines. The tips of these grounded electrodes can be inserted into the microdischarge 12 without altering the electrical operation of the SRR because the λ/4 length transforms the short circuit termination into an open circuit impedance within the active microplasma region. The SRR can then be biased relative to the grounded electrodes using a biasing-T 74 and a voltage source 13 as shown. This biasing scheme allows one to control the sheath width of the microplasma and to move particles within the trap or to expel particles from the trap.

As shown in FIG. 8, the SRR 70 is placed within a 6-way conflat chamber 81 (φ=2.5 cm). Gas is introduced within the chamber 81 through inlet 84 and removed by a pump 56 Microwave power 11 and the sheath control voltage 13 are applied through a bias tee 74 and a coaxial vacuum feedthrough 83. Test particles are introduced by a shaker 82 positioned approximately 2 cm from the microplasma. The shaker consists of an aluminum container filled with 1 μm diameter melamine particles. The particles exit the container through a 0.05" hole in the bottom (not shown). To reduce agglomeration of the particles, the exit hole is covered by a nickel mesh with 6 μm openings. The shaker is mounted on a linear feedthrough 85; tapping the linear feedthrough releases a few particles into the 6-way tee 81. Once trapped in the microplasma, the particles are illuminated by a HeNe laser 86 and observed at a 90° angle through a microscope with a long working distance. A 632 nm filter (not shown) is used to block the plasma emission when observing particles. A digital SLR camera mounted on the microscope is used to record the particle positions through observation window 88.

EXAMPLE III

Operation of the System of the Invention

Preliminary experiments demonstrate that the particles are indeed trapped by the potential gradients formed by the microplasma sheath. Most experiments were performed in 2 torr of argon with an absorbed power of 0.25 W. The microplasma is somewhat diffuse at this pressure, and the visible glow extends ~2 mm from the discharge gap. In the absence of intentional particle expulsion, particles are observed to remain within the microplasma for approximately 5 minutes, but may be trapped for substantially longer or shorter periods depending on gas flow, gas pressure and particle density.

Figure 9A:
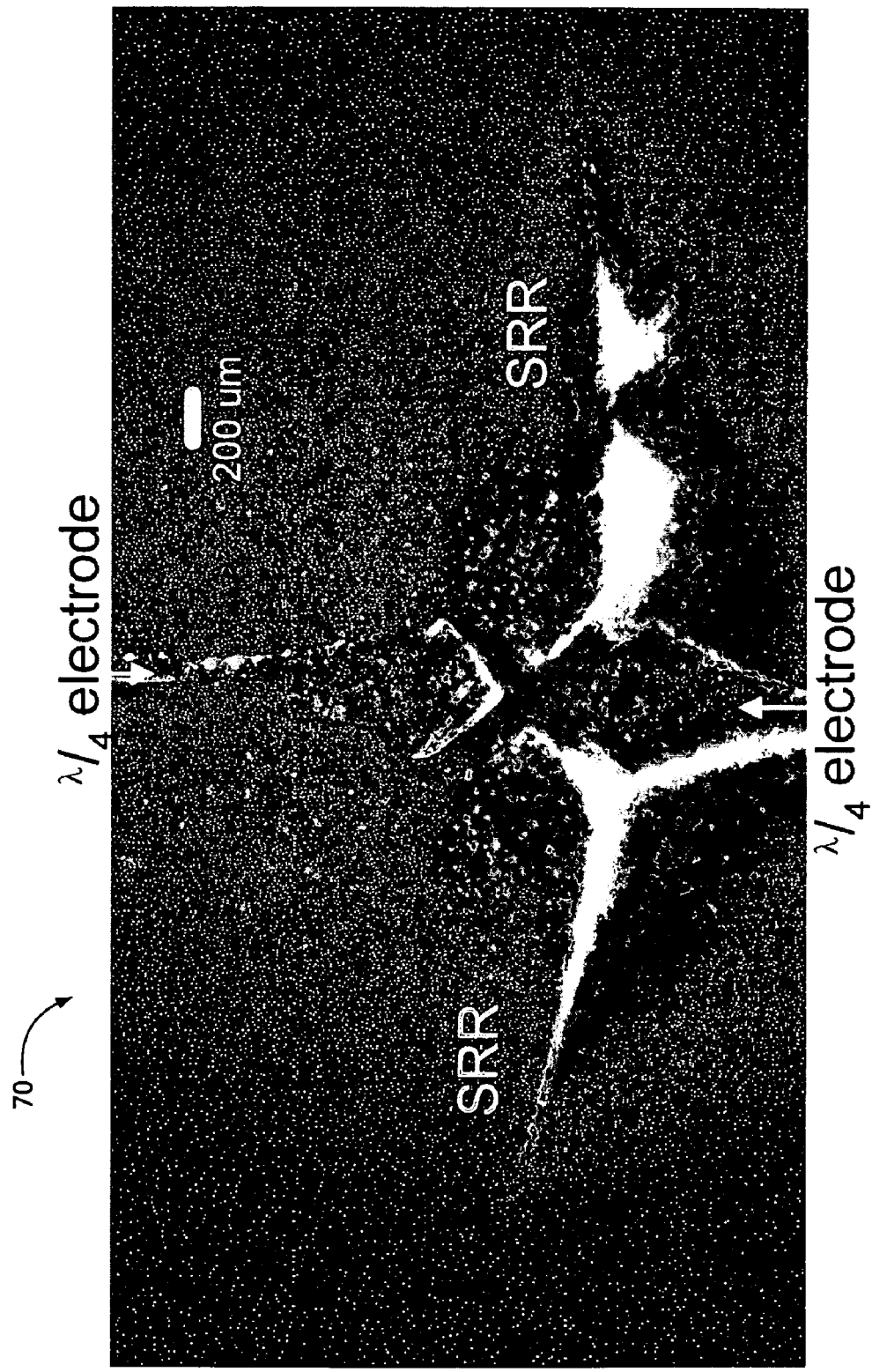
FIG. 9a is a micrograph of 1 µm melamine particles trapped within the SRR microplasma. The upper right quadrant shows a plasma crystal.

FIG. 9a is a micrograph of the particle trap. The grounded λ/4 auxiliary electrodes 72 enter from the top and bottom of the photograph. The microplasma is generated by the split ring resonator electrodes 15, which are also labeled "SRR".

Referring also to FIG. 8, a laser 86 illuminates the SRR from the bottom edge of the photo. Due to the laser light scattered from the microstrip transmission lines 15 and the dielectric substrate, the trapped microparticles 16 are most readily visible in the upper left and upper right quadrants. The exposure time for the photograph is 0.1 seconds, so particle motion is observed as streaking.

Figure 9B:
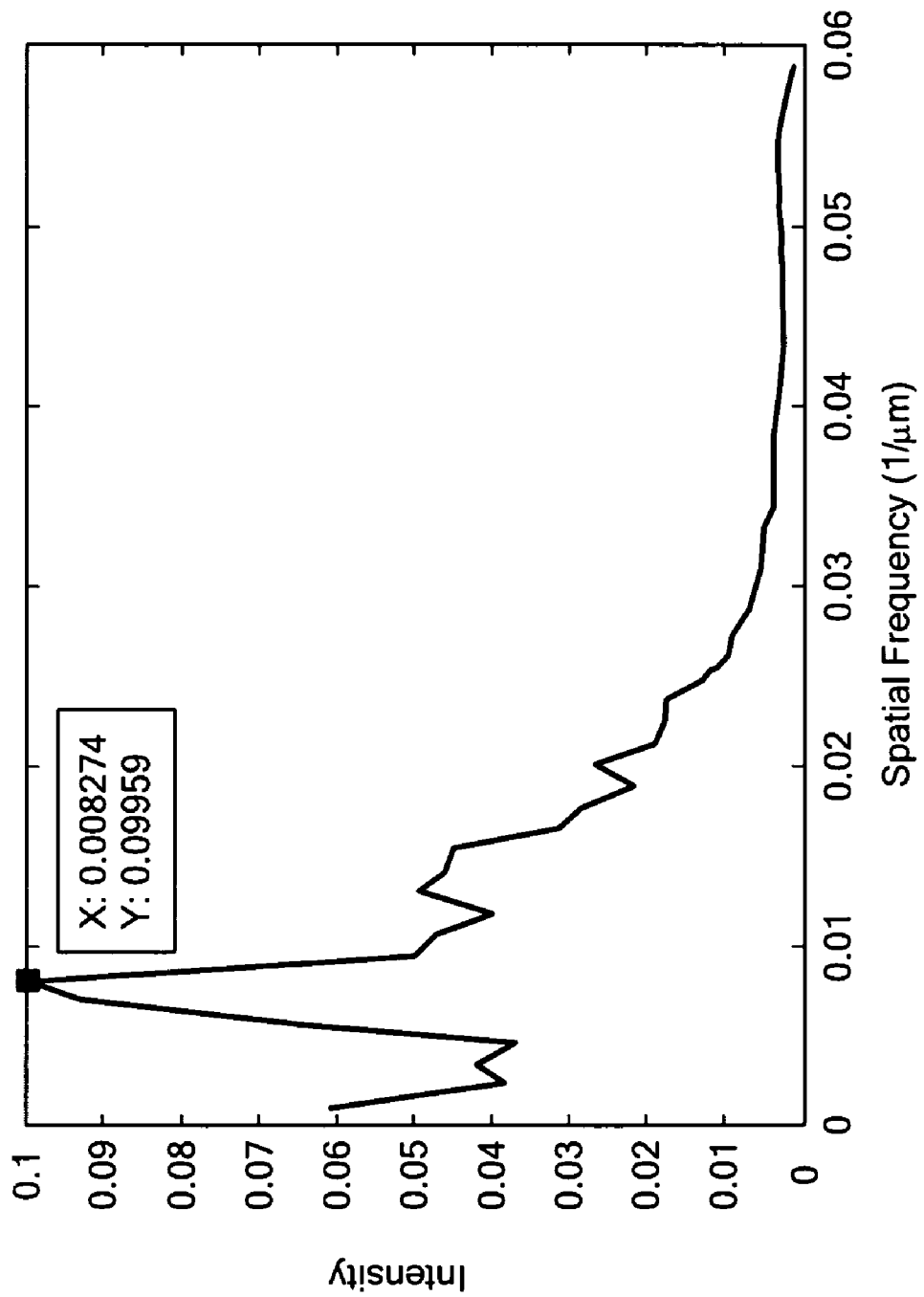
FIG. 9b is a plot of the data of FIG. 9a (intensity vs spatial frequency), from which it is calculated that the periodicity of the particles is 120 µm.

The upper right quadrant of FIG. 9a shows that the particles suspended above the dielectric layer 68 are exhibiting some self-organizing behavior, referred to as a plasma crystal.[18,19,20] A 2D Fast Fourier Transform (FFT) of the image was used to determine the spatial frequency of the particle positions. The φ-integrated FFT is plotted in the graph of FIG. 9b and shows that the spatial frequency of the particles is 0.0083 μm$^{-1}$, corresponding to an average separation of 120 μm.

Figure 10:
FIG. 10 shows particles are observed to orbit over the dielectric layer. The orbital period is less than the exposure time of the photo (0.1 s), making the particles appear as rings with orbital radii of 25-100 µm.

In addition to plasma crystal formation, one can also commonly observe orbiting particles within the microplasma trap 70. In the experiment shown in the micrograph of FIG. 10, there is no static magnetic field, and particles are observed to orbit independent of gas pumping. The particle orbits do not decay but appear to end abruptly upon collision with another particle. Several orbiting particles are highlighted in the upper left quadrant of FIG. 10. Measuring the orbital diameter and frequency of these particles may also provide a novel detection method.

Figure 7:
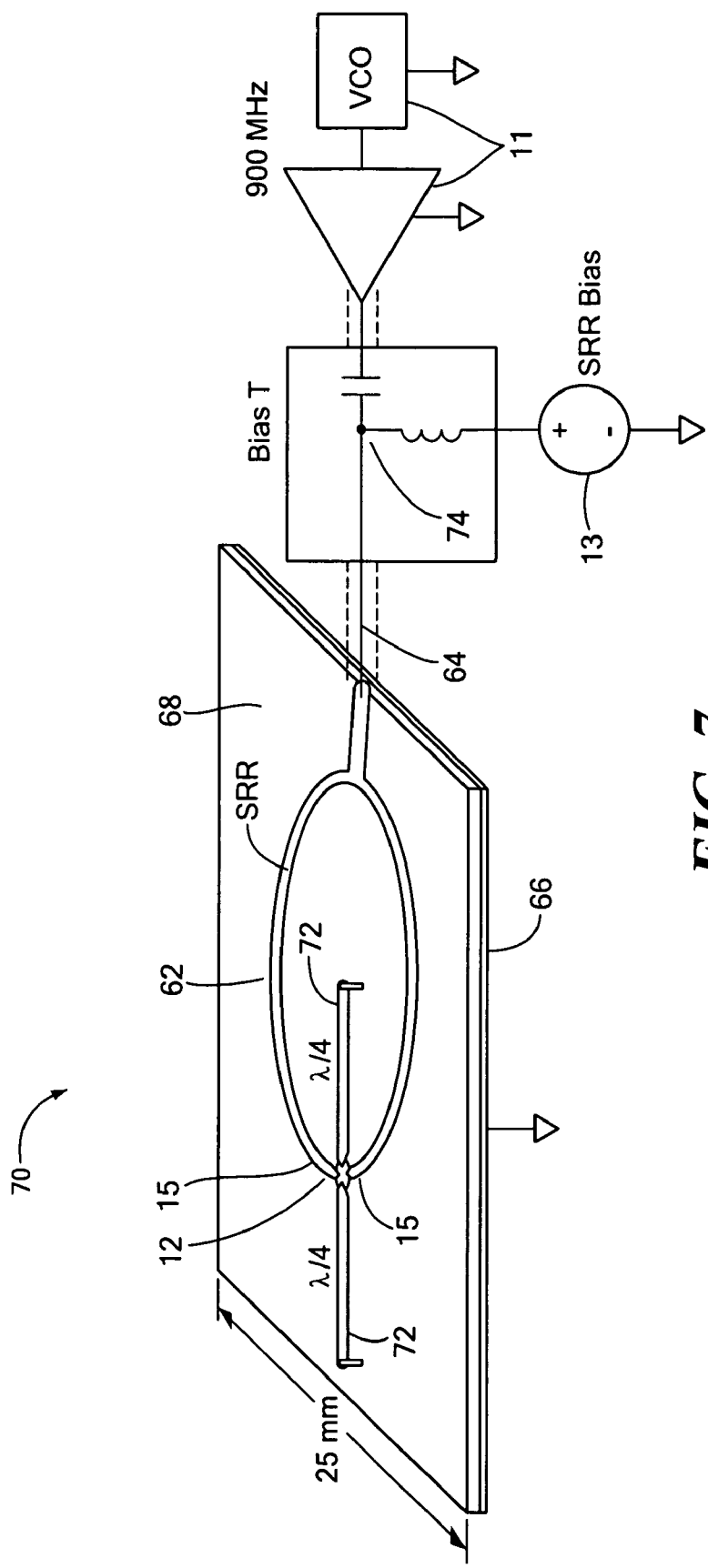
FIG. 7 shows the split-ring resonator with two grounded reference electrodes and a bias-T. The microplasma forms at the gap in the ring and overlaps the λ/4 reference electrodes.
Figure 11A:
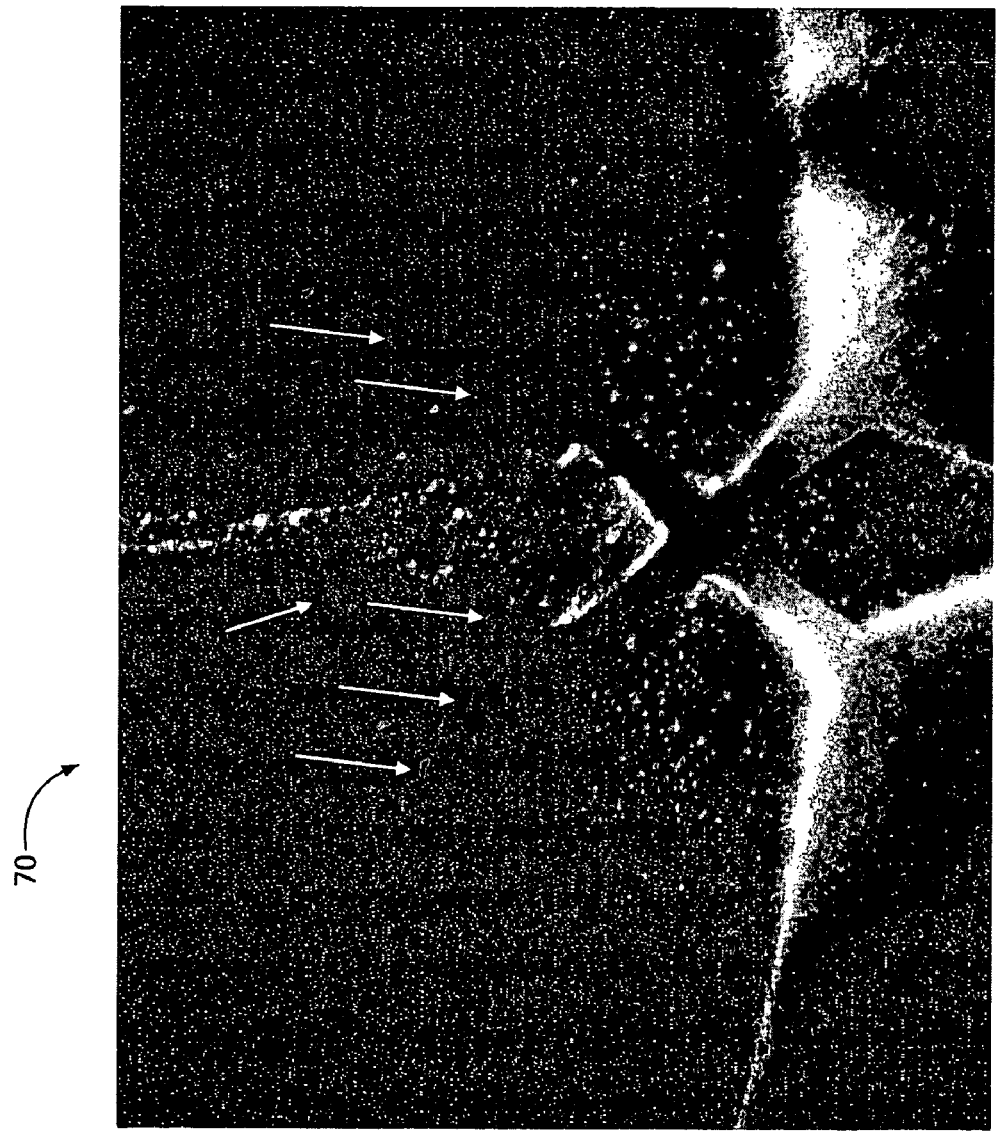
FIG. 11a is a micrograph showing 1 µm melamine particles being expelled from the microplasma trap by the application of a voltage pulse. Moving particles are highlighted by arrows and are shown streaking away from the grounded electrode.
Figure 11C:
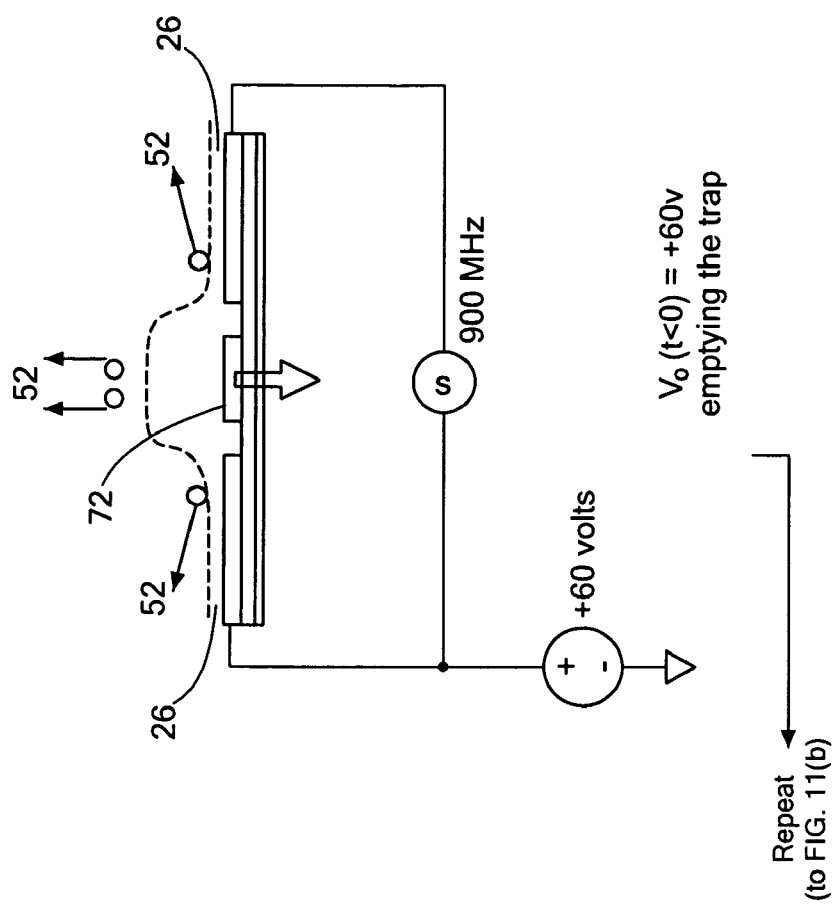
FIGS. 11b and 11c are cross section schematic side views of the microplasma of FIG. 11a showing the shape of the plasma sheath at t<0 and t>0, respectively.
Figure 11B:
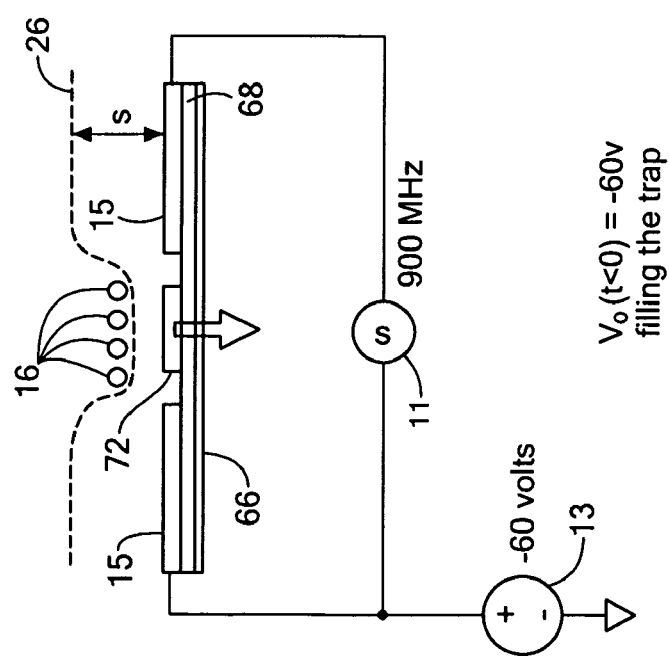

The microplasma sheath may be significantly expanded by applying a DC voltage to the SRR electrodes, using a biasing Tee (FIG. 7). FIG. 11a is a micrograph of microparticles in the process of being expelled from the microplasma trap 70 by applying a voltage pulse 13 to the SRR. FIGS. 11b and 11c illustrate schematically the trapping and expulsion of particles from the trap 70. For t<0, the SRR is biased at −60v, causing a wide sheath 26 to form adjacent to the microstrip electrodes 15. The sheath is narrow near the auxiliary electrode 72. The narrow region forms the electrostatic trap where trapped particles 16 reside. After t=0, the voltage pulse 13 is increased to +60 volts. This reduces the sheath 26 near the microplasma electrodes 15 and expands the sheath near electrode 72, as shown in FIG. 11c. The change in the potential shape expels the particles 52 from the trap. Those skilled in the art will recognize that the shape of the microplasma electrodes 15 and auxiliary electrodes 72 can be optimized to control the direction of particle expulsion such that the particles are directed towards a collection electrode where the particles are detected. At a potential of −60v, particles are repelled from the SRR through a distance of 700 μm. Assuming that this distance is the approximate sheath boundary, the microplasma density is ~10$^{10}$ cm$^{-3}$ at 0.25 W (2 torr, argon).

Thus, in summary, the ion sheath surrounding a split-ring resonator microplasma causes the discharge to behave as a 3D potential well. Particles are charged by electrons at distances of at least 2 cm from the central region of the microplasma; these particles are then electrostatically attracted toward the microplasma and trapped in its potential well. The particles are observed to retain charge long after the microplasma is extinguished, allowing for time-of-flight sorting and electrostatic collection.

REFERENCES

1. "Microplasmas for chemical analysis: analytical tools or research toys?" V. Karanassios, Spectrochimica Acta Part B 59 909-928 (2004).
2. "Alternative approach to nanocomposite synthesis by sputtering," G. M. Chow, R. L. Holtz, A. Pattnaik, and A. S. Edelstein, Appl. Phys. Lett. 56, 1853 (1990).
3. "Narrowing sputtered nanoparticle distributions," F. H. Kaatz, G. M. Chow, A. S. Edelstein, J. Mater. Res. 8, 995 (1993).

4. "Ultrafine metal particles," C. G. Granqvist and R. A. Buhrman, J. Appl. Phys, 47, 2200 (1976). (1-15 nm)
5. "The effects of electrostatic, molecular drag, and gravitational forces on the behavior of particle clouds in an RF discharge," J. F. O'Hanlon, J. Kang, L. K. Russell, and L. Hong, IEEE Trans. Plasma Sci. 22, 122, (1994).
6. "Size determination of nanoparticles in low-pressure plasma with laser-induced incandescence technique," G. S. Eom, C. W. Park, Y. H. Shin, K. H. Chung, S. Park, W. Choe, and J. W. Hahn, Appl. Phys. Lett. 83, 1261 (2003).
7. See for example, Model 3085, TSI Incorporated, Particle Instruments, Shoreview, Minn. 55126 U.S.A., at http://www.tsi.com/particle/downloads/manuals/1933792e-3080.pdf. Also see, *Investigation of the Aerosols Produced by a High-speed, Hand-held Grinder Using Various Substrates*," A. T. Zimmer and A. D. Maynard, Ann. Occ. Hyg. 46, 663 (2002).
8. "In Situ laser diagnostic studies of plasma-generated particulate contamination," G. S. Selwyn, J. Singh, and R. S. Bennett, J. Vac. Sci. Technol. A, 7, 2758 (1989).
9. "A particle-in-cell simulation of dust charging and shielding in low pressure glow discharges," S. J. Choi and M. J. Kushner, IEEE Trans. Plasma Sci. 22, 138 (1994).
10. "Transport of dust particles in glow-discharge plasmas," M. S. Barnes, J. H. Keller, J. C. Forster, J. A. O'Neill, and D. K. Coultas, Phys. Rev. Lett. 68, 313 (1992).
11. "On equilibrium states and dust charging in dusty plasmas," K. Ostriklo and L. Stenflo, IEEE Trans. Plasma Sci. 29, 175 (2001). Also, see P. K. Shukla, D. Mendis, and V. W. Chow, *The Frontiers of Dusty Plasmas.* Singapore: World Scientific, 1996.
12. "Plasma Assisted Deposition," J. Hopwood, in *Handbook of Nanophase Materials*, A. Goldstein, ed., Chapter 6, pp. 141-198 (Marcel Dekker, New York, 1997).
13. "The location of very small particles in silane rf discharge", K. Rozsa, G. Bano, and A. Gallagher, IEEE Trans. Plasma Sci. 29, 256 (2001).
14. "Low-power microwave plasma source based on a microstrip split-ring resonator," F. Iza and J. Hopwood, *IEEE Transactions on Plasma Science*, Vol. 31(4), pp. 782-787 (2003).
15. M. A. Lieberman and A. J. Lichtenberg, *Principles of Plasma Discharges and Materials Processing*, p. 528 ff., (Wiley, New York, 1994).
16. F. Iza and J. Hopwood, Plasma Sources Science and Technology 14, 397-406 (2005).
17. G. S. Selwyn, J. Singh, and R. S. Bennett, J. Vac. Sci. Technol. A 7, 2758ff (1989).
18. G. A. Hebner, M. E. Riley, D. S. Johnson, Pauline Ho, and R. J. Buss, "Direct Determination of Particle-Particle Interactions in a 2D Plasma Dust Crystal," Phys. Rev. Lett. 87, 23ff (2001).
19. H. Thomas, G. E. Morfill, V. Demmel, J. Goree, B. Feuerbacher and D. Mohlmann, Phys. Rev. Lett. 73, 652ff (1994).
20. Vivek Vyas, Gregory A. Hebner, and Mark J. Kushner, J. Appl. Phys. 92, 6451ff (2002).

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A system for detection of particles in a gas, said system comprising:
    a trap comprising a microplasma generator that provides a microplasma, said microplasma configured to receive a sample of said gas so that the particles in the vicinity of said microplasma become trapped and concentrated within said microplasma; and
    a particle sensor that measures at least one of the particle count and the size distribution of said particles in said gas.
2. The system of claim 1, wherein said microplasma generator is a low power generator.
3. The system of claim 1, wherein said microplasma generator is portable.
4. The system of claim 1, wherein said microplasma generator comprises a split-ring resonator.
5. The system of claim 1, wherein said microplasma generator is a miniature inductively coupled plasma generator.
6. The system of claim 5, wherein said microplasma generator is a monolithic inductively coupled plasma generator.
7. The system of claim 1, wherein said particle sensor detects collected particles by charge.
8. The system of claim 1, wherein said particle sensor is a scattering laser detector.
9. The system of claim 1, wherein said particle sensor is a differential mobility detector.
10. The system of claim 1, wherein said particle sensor detects collected particles by light emissions from said particles or from atoms and molecules eroded from said particles.
11. The system of claim 1, wherein said system traps and measures particles having a radius less than approximately 50 nm.
12. A method of trapping and detecting particles in a gas phase, said method comprising the steps of:
    providing a microplasma generator;
    forming a microscopic glow discharge (microplasma) with said generator;
    feeding said microplasma with a sample of gas from said gas phase, wherein particles in the vicinity of said microplasma become negatively charged, trapped and concentrated within said microplasma;
    detecting said particles trapped within said microplasma to determine at least one of particle count and size distribution of said particles.
13. The method of claim 12, wherein said detecting step comprises the steps of:
    applying a voltage waveform to said microplasma; and
    collecting charged particles emptied from said microplasma by said voltage waveform on an electrode.
14. The method of claim 13, wherein said waveform is a pulse, a ramp or a sinusoid.
15. The method of claim 12, wherein said detecting step comprises the steps of:
    modulating power supplied to said microplasma generator, wherein said microplasma dissipates; and
collecting charged particles emptied from said dissipated microplasma on an electrode.
16. The method of claim 15, wherein, in said modulating step, said power is turned off.
17. The method of claim 12, wherein at least some of said trapped and detected particles have a radius that is less than approximately 50 nm.

* * * * *

UNITED STATES PATENT AND TRADEMARK OFFICE
CERTIFICATE OF CORRECTION

| | | |
|---|---|---|
| PATENT NO. | : 7,728,253 B2 | Page 1 of 1 |
| APPLICATION NO. | : 11/478348 | |
| DATED | : June 1, 2010 | |
| INVENTOR(S) | : Jeffrey A. Hopwood | |

It is certified that error appears in the above-identified patent and that said Letters Patent is hereby corrected as shown below:

Column 9, line 20, "particles are" should read --particles 16 are--; and

Column 10, line 66, "gap) (170°"" should read --gap (170°)--.

Signed and Sealed this
Twenty-sixth Day of April, 2011

David J. Kappos
*Director of the United States Patent and Trademark Office*